(12) United States Patent
Thielen et al.

(10) Patent No.: US 8,808,237 B2
(45) Date of Patent: Aug. 19, 2014

(54) EXPANDABLE PERFUSION BALLOON

(76) Inventors: Joseph Michael Thielen, Buffalo, MN (US); William Joseph Drasler, Minnetonka, MN (US)

(*) Notice: Subject to any disclaimer, the term of this patent is extended or adjusted under 35 U.S.C. 154(b) by 97 days.

(21) Appl. No.: 13/066,717

(22) Filed: Apr. 23, 2011

(65) Prior Publication Data
US 2011/0264039 A1 Oct. 27, 2011

Related U.S. Application Data

(60) Provisional application No. 61/343,244, filed on Apr. 26, 2010, provisional application No. 61/460,953, filed on Jan. 10, 2011.

(51) Int. Cl.
*A61M 29/00* (2006.01)
*A61M 31/00* (2006.01)
*A61M 37/00* (2006.01)
*A61M 25/10* (2013.01)

(52) U.S. Cl.
CPC ..... *A61M 25/104* (2013.01); *A61M 2025/1081* (2013.01); *A61M 2025/1075* (2013.01); *A61M 2025/105* (2013.01); *A61M 2025/1095* (2013.01); *A61M 2025/1084* (2013.01); *A61M 2025/1093* (2013.01)
USPC ............. 604/103.06; 604/101.02; 604/103.09

(58) Field of Classification Search
USPC .................. 604/101.01, 101.02, 103, 103.02, 604/103.06, 103.09
See application file for complete search history.

(56) References Cited

U.S. PATENT DOCUMENTS

| | | | | |
|---|---|---|---|---|
| 4,706,670 | A * | 11/1987 | Andersen et al. | 606/195 |
| 5,112,304 | A * | 5/1992 | Barlow et al. | 604/103.09 |
| 5,201,706 | A * | 4/1993 | Noguchi et al. | 604/103.12 |
| 6,398,792 | B1 * | 6/2002 | O'Connor | 606/128 |
| 6,629,952 | B1 * | 10/2003 | Chien et al. | 604/103.09 |
| 2002/0193820 | A1 * | 12/2002 | Wakuda et al. | 606/194 |
| 2004/0260239 | A1 * | 12/2004 | Kusleika | 604/101.2 |
| 2009/0038752 | A1 * | 2/2009 | Weng et al. | 156/276 |

* cited by examiner

*Primary Examiner* — Nathan R Price

(57) ABSTRACT

A balloon catheter for dilation of stenotic tissue within a tubular member of the body such as a blood vessel provides fluid flow such as blood flow through the balloon while it is being inflated and after it has been inflated. For valvuloplasty applications or for predilitation prior to a TAVI procedure the balloon is placed across the stenotic aortic valve leaflets and inflated to push the leaflets aside to create a greater blood flow area or allow improved subsequent passage of the large TAVI catheter across the stenotic aortic valve leaflets. As the balloon is inflated in diameter, it is required to reduce in length; this length reduction causes a braided inner tubing to also reduce in length. The braided inner tube is thereby required it to increase in diameter during the balloon inflation and create a suitably large blood flow path through the inner tubing. The continuous perfusion through the inner tubing of the balloon allows greater balloon inflation times, improved valvular dilation, and obviates the need for rapid pacing during the valvuloplasty procedure.

15 Claims, 7 Drawing Sheets

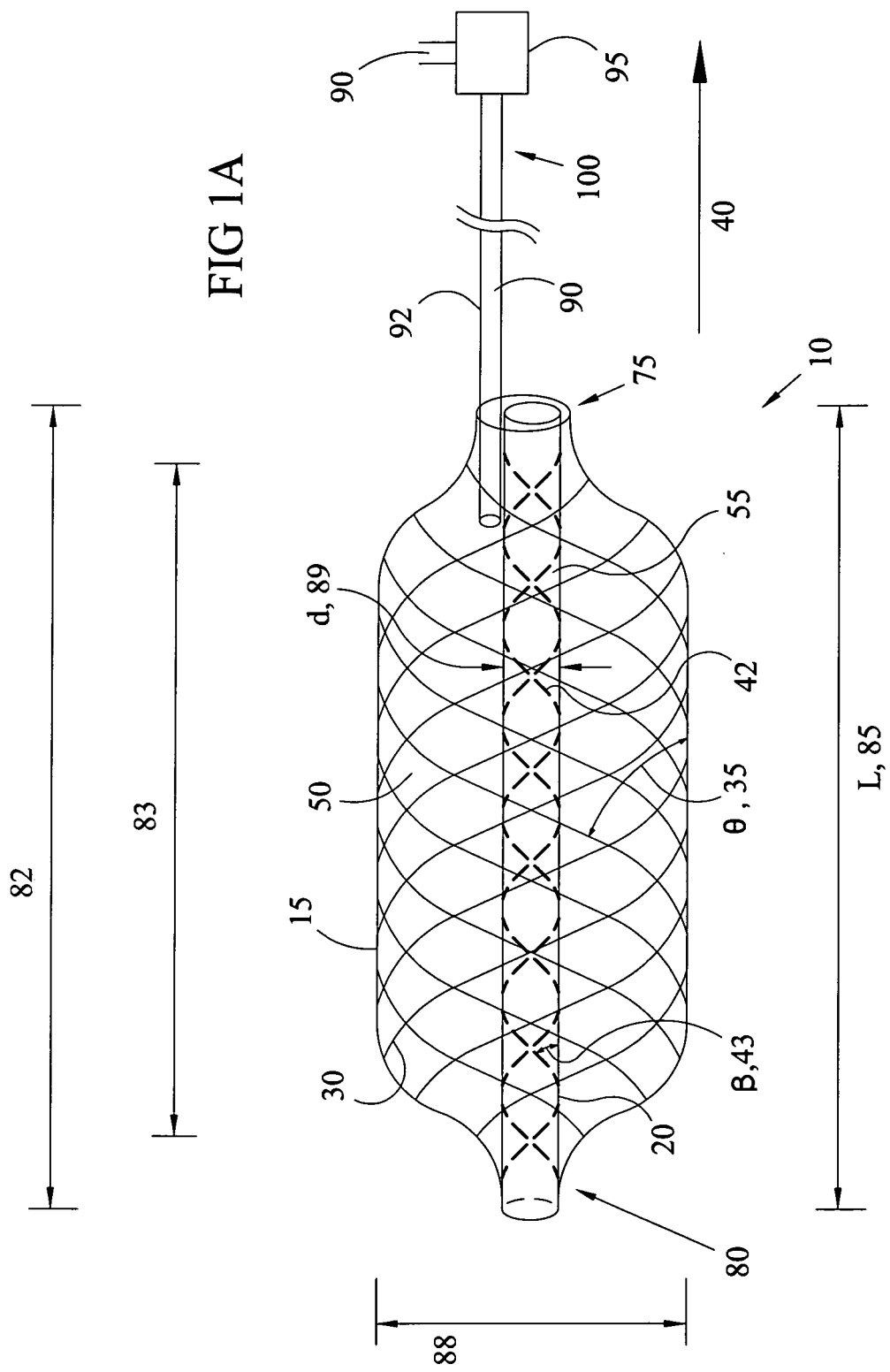

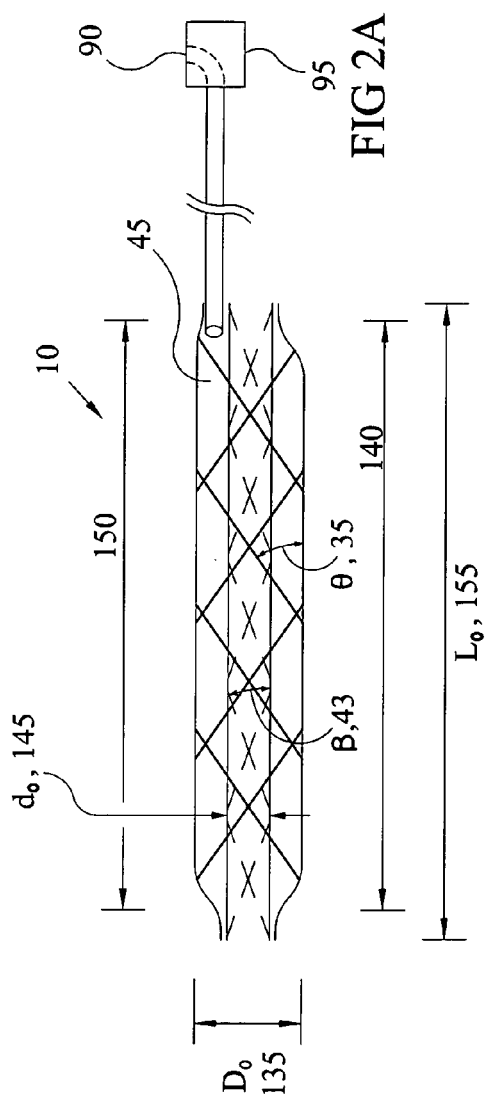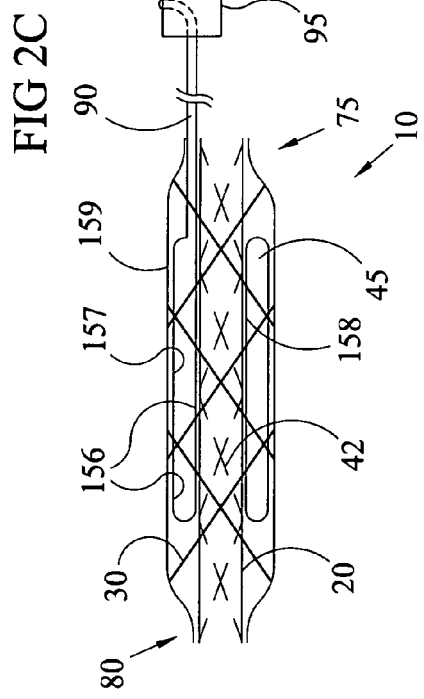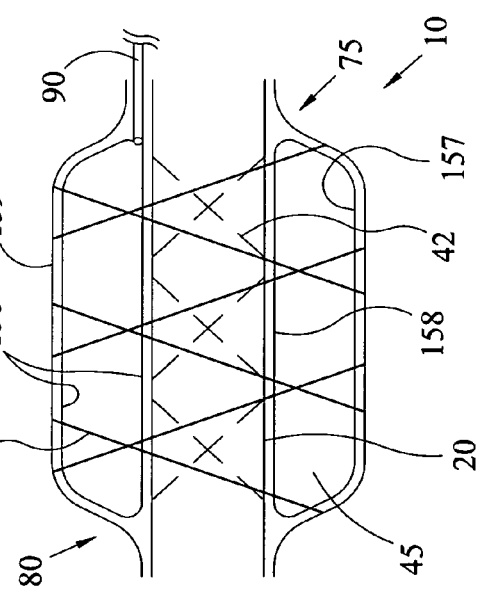

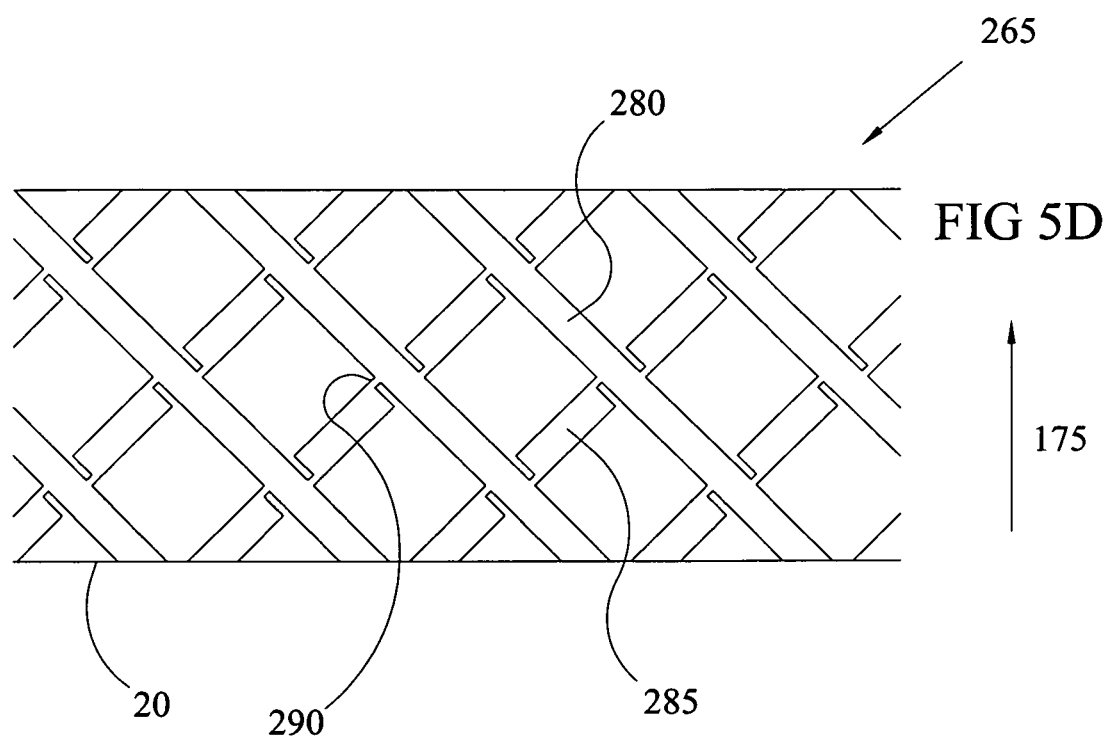

EXPANDABLE PERFUSION BALLOON

CROSS REFERENCE TO RELATED APPLICATIONS

This patent application claims priority to U.S. Provisional Application Ser. No. 61/343,244 entitled Braided Perfusion Balloon by Joseph M. Thielen filed 26 Apr. 2010, and priority to U.S. Provisional Application Ser. No. 61/460,953 entitled Expandable Perfusion Balloon by Joseph M. Thielen and William J. Drasler filed 10 Jan. 2011, both of which provisional applications are hereby incorporated herein by reference in their entirety.

FIELD OF THE INVENTION

This invention relates to an interventional catheter that is placed into a lumen of the body in a smaller diameter configuration and is expanded to a larger diameter configuration in apposition with the lumen while maintaining passage for flow of fluid through the lumen.

BACKGROUND OF THE INVENTION

Providing expansion or enlargement to blood vessels and other tubular organs of the body including coronary arteries and veins, peripheral arteries and veins, the aorta, the aortic root, and the left ventricular outflow tract is often accomplished with a balloon catheter or other dilating catheter having an expansion balloon or other expanding member that places the expanding member into contact with the tubular member of the body. Often an expanding member is a dilatation balloon that is introduced in a smaller diameter configuration and is expanded in situ to cause a narrow portion in the tubular member to become enlarged in diameter. This angioplasty or vessel reforming procedure is accomplished to enlarge the stenosis found in coronary, peripheral, or other vessels of the body and thereby provide a larger lumen for blood or fluid flow and improve perfusion or fluid delivery to the tissue being supplied by the vessel. In a similar manner valvuloplasty is performed using a catheter with a balloon near its distal end to expand the diseased and stenotic aortic valve leaflets or other valve leaflets of the heart in order to allow improve blood flow through a specific valve or as a predilitation before the implantation of a percutaneously implanted valve. The catheter is generally introduced through the femoral artery and is advanced in a small diameter configuration across the aortic valve leaflets such that a portion of the balloon resides within the aortic sinus and a portion also can reside in the left ventricular outflow tract. The balloon is inflated into contact with the leaflets and thereby push or expand the leaflets outward into contact with the wall of the aortic sinus region. Such extension of the aortic valve leaflets allows the valve to open to provide a greater flow area. Alternately, in the case of predilitation prior to trans-catheter aortic valve implantation (TAVI), the aortic valve leaflets have been properly conditioned or expanded to receive the trans-catheter implant of a stented aortic valve. Other vessels of the body that could be dilated include the lymphatic vessels, esophagus, trachea, the intestinal tract, bile ducts, the urinary tract, or other tubular members of the body.

During the angioplasty or valvuloplasty procedure using a balloon dilatation catheter, blood flow across the inflated balloon is blocked thereby preventing the normal flow of blood through the tubular member of the body. For the case of coronary angioplasty, blood flow to the distal coronary tissue bed can be temporarily halted during balloon inflation resulting in lack of proper oxygen delivery to the myocardium. The myocardium can only survive for a period of several minutes without oxygen before tissue damage can occur. For the case of aortic valvuloplasty, blood flow from the left ventricle of the heart is temporarily blocked by the inflated balloon resulting in a reduced oxygen delivery to the brain, the heart, and other tissues of the body. The brain cannot function adequately if it is deprived of blood-carrying oxygen for period of only 15-30 seconds. Therefore, during such valvuloplasty procedures, balloon inflation must be maintained for only a short period of time.

It is the purpose of the present invention to provide an interventional catheter with a valvuloplasty balloon that will allow perfusion of blood to occur while the balloon is inflated to dilate the valve leaflets. A similar but smaller diameter device could be used to provide perfusion to the coronary arteries. A similar but proportionately sized interventional perfusion balloon catheter could be used to allow perfusion to any tubular member of the body while the balloon is inflated. Alternately, the distal expanding member of the device need not be a balloon, but could be expanded via mechanical means. The present invention allows a small diameter catheter to be inserted either percutaneously or via trans-catheter access across a stenotic or narrowed region of a tubular body member. As the expandable member is enlarged to dilate a stenotic region, perfusion of body fluid through the tubular member of the body is maintained.

SUMMARY

The present invention is well suited to use as an interventional catheter having a perfusion balloon for performing valvuloplasty or predilitation prior to TAVI. Although the discussion will be primarily directed to this application, it is understood that the invention can be applied to smaller blood vessels such as coronary or peripheral arteries or veins by making the balloon proportionately smaller in diameter and adjusting the perfusion lumen diameter to provide the necessary oxygen delivery to the body tissues. Also, it is understood that the device can be applied to other tubular members of the body that require contact with or expansion of the wall of the tubular member of the body while providing perfusion of material through the perfusion lumen of the invention. The distal balloon could also be detached from the perfusion catheter in a manner similar to detachable balloons used for the intention of vessel occlusion. The perfusion balloon could then be positioned within a tubular member of the body and detached to provide a passage for flow of fluid though the body vessel.

The invention is primarily directed toward an interventional catheter having a dilatation balloon positioned at or near its distal end. The balloon is an outer expandable member; one embodiment has braided filaments located within its wall and extending throughout a substantial portion of the balloon surface. The braided filaments extend preferably throughout the entire balloon surface. A flexible polymer generally surrounds the braided filaments to form the balloon wall of the balloon to form a continuous fluid-tight surface. Located concentrically within the balloon and extending generally from one balloon end to another is an inner expandable member which in one embodiment is a braided inner tubing that serves as a perfusion tube that provides a perfusion lumen. The braided tubing is coated with a flexible polymer to provide a fluid-tight surface. The inner surface of the braided balloon is joined to the outer braided surface of the inner tubing along a portion of the surfaces near their ends. The annular space that is formed between the balloon surface and the inner tubular surface can then be inflated using saline or contrast medium. A catheter shaft containing an inflation lumen is attached to the distally located perfusion balloon and provides fluid communication from the proximal end of the catheter to the perfusion balloon for inflation of the annular space.

The angle of the braided filaments found in the balloon is chosen such that upon inflation of the balloon, the inflation pressure causes the balloon to expand in diameter while the balloon length is forced to reduce due to the presence of the braid. The lower the angle of the braided filaments with respect to the axis of the balloon the greater the force acting to shorten the balloon. Since the balloon is attached to the inner tubing, the expansion force from the balloon will act to shorten the length of the inner tubing. The braided filaments of the balloon therefore are structural in the respect that they cannot stretch during the perfusion balloon inflation and must instead transfer the expansion force of the balloon wall into a force that reduces it in length.

The braided fibers found in the inner tubing are braided with an angle that causes the inner tubing to increase in diameter when it is forced to reduce in length. The braided fibers of the inner tubing also serve to prevent the inner tubing from collapse or buckling due to the external pressure found in the annular space around the inner tubing. The braided fibers of the inner tubing are therefore structural fibers that provide support to the inner tubing against crushing or buckling. As the inner tubing is exposed to the inflation pressure, this generates a force that generally creates a tendency for the inner tubing to reduce in diameter and increase in length; however, since the surface area of the inner tubing is smaller than the balloon, the inner tubing and the balloon will both shorten in length due to the inflation pressure and the perfusion balloon will increase in diameter.

The joined end regions of the annular space located between the balloon and the tubing also generates a force across the balloon and tubing that has a tendency to cause the perfusion balloon to increase in length while getting smaller in diameter. The large surface area of the balloon, however, is able to generate enough force acting to reduce the length of the balloon and inner tubing to overcome the forces applied to the joined end regions of the annular space acting to increase the length. The result is that inflation of the perfusion balloon results in shortening of the balloon and tubing length and an increase in diameter of both the balloon and inner tubing. As the inner tubing expands in diameter, it provides an increased flow area for perfusion of fluid such as blood while the balloon is performing its function of expanding the aortic valve leaflets or opening up a narrow region in a tubular member.

An alternate embodiment for the perfusion balloon has a floating annular balloon or bladder that is contained between a braided inner tubing and a braided outer tubing or balloon. The annular-shaped balloon can be formed from standard dilation balloon materials that achieve a predesignated diameter upon inflation. In this embodiment, the annular balloon could be folded to form its small diameter configuration. During deployment to a larger diameter configuration the annular balloon would not be required to reduce in length although it is possible for this to occur without deviating from the present invention. The floating annular balloon need not be attached to either the braided outer tube or the braided inner tubing although attachment sites can be formed from the annular balloon to either the inner or outer tubing without deviating from the present invention.

Providing perfusion while the tubular member of the body is being expanded can provide significant benefits and options to the physician or operator. The dilating procedure can be extended in time without causing damage to tissue normally being perfused by the tubular member because the tissues would be continuously supplied with necessary oxygen and other nutrients. Also, since most tissues of the body are viscoelastic, it has been observed that exposure to longer periods of dilatation can help allow the stenotic tissue including stenotic heart valves to extend out and result in greater durability of the valvuloplasty or angioplasty procedure thereby extending the therapeutic benefit for the procedure. Improved durability can be the result of slower stretching or altered fracture mechanisms of fibrous connections that would have a greater tendency to remain extended following the valvuloplasty or angioplasty procedure with the perfusion balloon.

One additional embodiment of the present invention includes placing a temporary valve within the inner lumen of the perfusion tubing. The valve can be a simple duck-bill, bileaflet valve, a monoleaflet, or trileaflet valve that is placed in the tubing lumen to ensure that blood flow is directed in an antegrade direction as intended by the normal blood flow direction. The structure of such valves can be similar to collapsible valves used in the venous and arterial system of the body.

In another embodiment, the annular space can be heated by electrical means or by heated fluid supplied from a source external to the body and delivered to the annular space via the catheter shaft. This heated perfusion balloon would allow the fibrous tissue to reduce in viscosity thereby allowing fibrous tissue such as fibrotic valves to extend to a greater extent and with greater durability thereby extending the length of time that the valve leaflets remain flexible and functional.

Additionally, heat can be supplied directly from an electromagnetic radiation source located within the perfusion balloon and absorbed directly into the tissue to cause heating or fracture of the tissue found in the valve leaflets or stenotic tissue of a tubular body member. One could provide laser energy, radio frequency energy, or other electromagnetic energy from a source located within the perfusion balloon or on the outside surface of the perfusion balloon.

In yet another embodiment liquid nitrous oxide, liquid carbon dioxide, or other cryogenic medium can be delivered to the perfusion balloon and can be caused to form a joule-kelvin expansion within the perfusion balloon and result in a cooling of the perfusion balloon. Such cryogenic therapy can cause the tissues of the heart leaflet or stenotic tissues to undergo greater microfractures while being expanded by the dilatation balloon. The presence of greater microfractures has been shown to generate greater durability for angioplasty when performed in peripheral vessels of the leg.

In still yet another embodiment, ultrasound energy can be directed outward toward the valve leaflets or fibrotic tissue to break up calcified portions of the leaflet or stenosis or densely fibrotic tissues. An ultrasound transducer place within the perfusion balloon or on the outside surface can direct its energy into vibration of the fibrotic or calcified tissue. The ultrasound transducer system can focus ultrasound energy if desired onto a specific region of the tubular member of the body. The ultrasound device can also be used to identify the shape and diameter of structures such as luminal diameter to improve the sizing of such lumens prior to implantation of a stent or stented valve.

In a further embodiment, a positive displacement pump such as a piston pump can be connected to the inflation lumen of the perfusion catheter. The piston can be advanced and withdrawn via a cam to generate a pulsatile or vibratory pressure pulse within the perfusion balloon. The rapid generation of pressure pulses can act to create fractures in calcified or hard fibrotic material such as that found in diseased valve leaflets or in some types of atherosclerotic plaque.

In a yet further embodiment, a drug such as Taxol or Sirolimus can be applied to the outside of the perfusion balloon prior to dilation against the vessel wall or the diseased leaflets of the aortic valve. The increased time for exposure of the tissue to the drug while the perfusion balloon is inflated will allow the drug to more effectively penetrate into the tissue.

In another embodiment, the outer expandable member of the perfusion balloon can be formed from a slotted elastic metal or plastic tube that is machined to form struts such that the slotted tube can mimic the diametric expansion and length reduction found in a braided tube. The slotted openings between the struts would be coated with an elastomeric polymer to ensure a fluid-tight wall structure. Similarly, the inner expandable member of the inner tube can be formed from a slotted elastic metal or plastic tube that has been coated with an elastomeric polymer. The slotted pattern has a hinge-like connection.

BRIEF DESCRIPTION OF THE DRAWINGS

FIG. 1A is a partially sectioned view of one embodiment of the perfusion balloon catheter in an expanded configuration.

FIG. 2A is a partially sectioned view of an embodiment of the perfusion balloon catheter in a non-expanded small diameter configuration.

FIG. 2B is a partially sectioned view of an embodiment of the perfusion balloon in an expanded or large diameter configuration.

FIG. 2C is a partially sectioned view of an embodiment of a non-expanded perfusion balloon.

FIG. 5D is a plan view of structural tubing fibers a portion of which have hinges.

DETAILED DESCRIPTION OF THE INVENTION

Figure 1B:
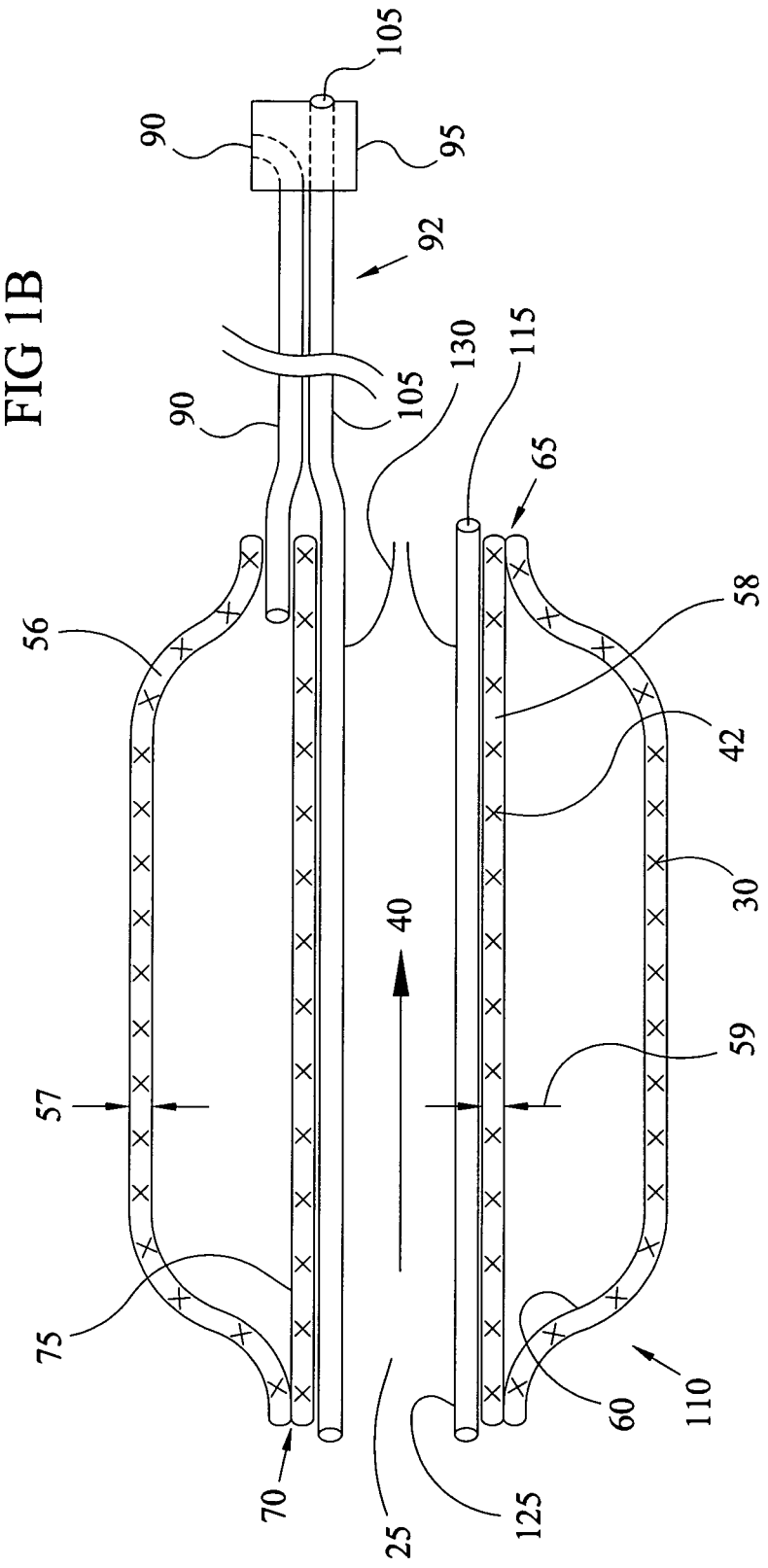
FIG. 1B is a partially sectioned view of an embodiment of the perfusion balloon catheter in an expanded configuration having a separate guidewire lumen and an adjunct lumen.
Figure 3A:
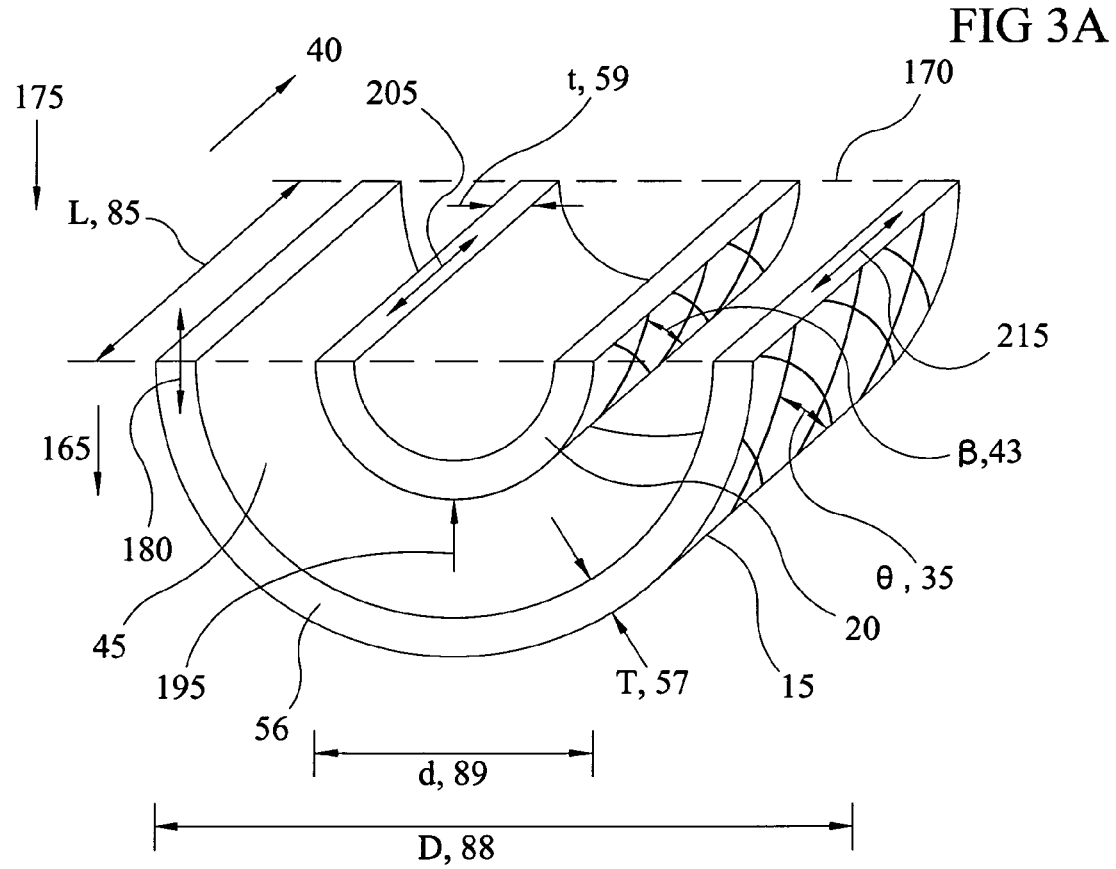
FIG. 3A is a perspective view of the outer balloon and inner tubing of an embodiment of the perfusion balloon.
Figure 3B:
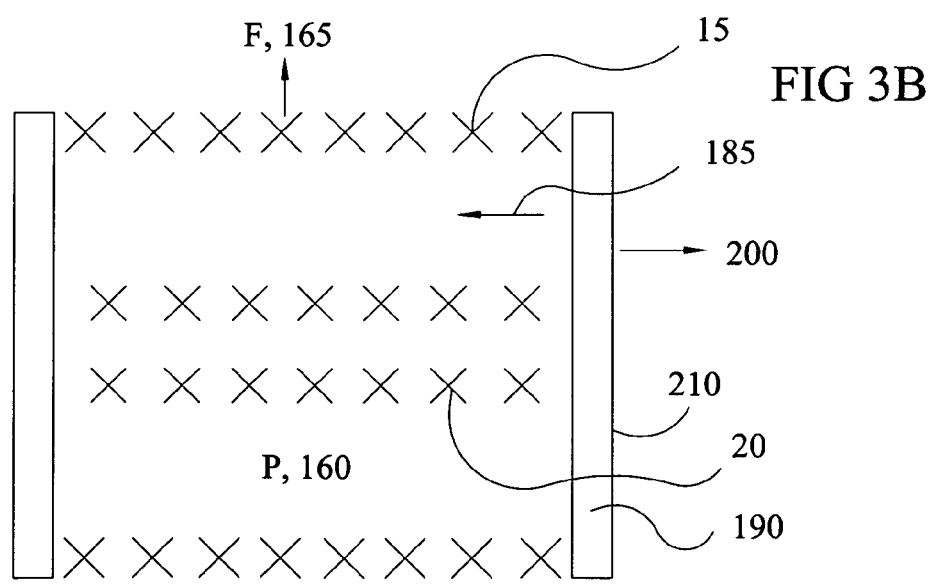
FIG. 3B is a sectional diagram of the outer balloon and inner tubing of an embodiment of the perfusion balloon.

The present invention is an interventional catheter having a perfusion balloon (10) located at or near its distal end. The perfusion balloon (10) is comprised of an outer balloon (15) and an inner tubing (20) that provides one embodiment of the perfusion lumen (25) as shown in FIGS. 1A and 1B. In this embodiment, the outer balloon or outer tubing (15) is braided with balloon filaments (30) at a balloon filament angle (35), Theta ($\theta$), with respect to the axial direction (40) and the inner tubing (20) has braided tube fibers (42) braided at tube fiber angle (43), Beta, ($\beta$) with respect to the axial direction (40). The inner tubing (20) is positioned within the outer balloon (15) forming an annular space (45) located between the outer tubing or outer balloon (15) and the inner tubing (20). The outer balloon filaments can be braided as shown in FIGS. 1A-1B however it is understood that any angled filaments formed from a spiral or machined tubing can also be used to form the perfusion balloon of the present invention. Similarly the inner tubing can be formed from angle fibers that are not required to be braided.

An elastomeric polymer, thermoplastic elastomer, or other flexible polymer is coated or otherwise applied, sprayed, dipped, or extruded onto the braided balloon filaments (30) and the braided tube fibers (42) to form a fluid-tight balloon polymeric surface (50) or coating and tube polymeric surface (55) or coating, respectively. The polymer can be silicone, polyurethane, copolymers, or other polymer that can stretch to accommodate length and diameter changes for the outer balloon (15) and inner tubing (20). The polymer can either bond to the balloon filaments (30) or tube fibers (42) or surround them to form an attachment with them. The outer balloon (15) wall can have an outer balloon wall thickness (57) that can range from less than 0.001 inch to more than 0.008 inches.

The outer balloon filaments (30) require that as the outer balloon (15) enlarges in diameter the outer balloon (15) will reduce in length. The braided balloon filaments (30) can be formed of a multifilament yarn that is very flexible and strong but has a very low profile and can bend easily. Such filaments can include Dacron, high molecular weight polyethylene, Kevlar, and others. The diameter of such multifilament yarns can range from less than 0.001 inch to approximately 0.003 inch. A monofilament member can also be used as the outer balloon filament (30). The balloon filaments (30) must be structural such that during expansion of the outer balloon, the balloon filaments (30) do not stretch, they must pivot easily at braid crossover points or points of braid contact, must force the outer balloon (15) to reduce in length as it increases in diameter, and must pull the inner tubing (20) inward into compression so that the inner tubing (20) also reduces in length. The inner tubing wall (58) has an inner tubing wall thickness (59) with a similar range to that of the outer balloon (15) and can be constructed of similar materials to the outer balloon (15).

The tube fiber has several structural requirements in order for it to function properly; the tube fiber must force the braided inner tubing (20) to shorten in length and increase in diameter as it is pulled inward from each end as a result of the length reduction of the larger outer balloon (15) during inflation. Additionally, the tube fiber has the structural requirement that it must provide the inner tubing (20) with resistance to collapse due to fluid pressure (160) contained in the annular space (45) during inflation of the perfusion balloon (10). The braided tube fiber can be made from monofilament polymer such as Dacron, polyethylene, Kevlar, or other polymers. Alternately, a metal fiber can be used to braid the inner tubing (20) to provide the support against buckling of the fiber and still provide a low profile. Such metals fibers include stainless steel, Nitinol, Cobalt-Chrome alloys and other metal alloys. It is anticipated that two different types of fibers could be interbraided or used to form the braid for the inner tubing (20).

A structural fiber such as a monofilament can be used to resist buckling of the inner tubing (20) while a smaller and more flexible multifilament fiber can be interbraided or used along with the monofilament to provide support for the flexible tube polymer surface that forms the fluid-tight inner tubing wall (58). The diameter for the monofilament fiber could range from 0.001 inch to 0.005 inch. The use of a flat fiber for the braid of the inner tubing (20) is also contemplated to provide improved profile while maximizing the support provided by the tube fibers (42) to resist collapse or buckling of the tube fiber due to the fluid pressure (160) found in the annular space (45). One could also use a double-coiled structure with each coil wound in a different direction to replace the braided tube fiber of the inner tubing (20) provided that the flexible tube polymer surface prevented slippage of one coil with respect to the other at cross-over points of the braid.

The inner surface (60) of the outer balloon (15) has a proximal attachment (65) and a distal attachment (70) via adhesive, thermal bonding, or other means to the outer surface of the inner tubing (20) at or near the perfusion balloon proximal end (75) and perfusion balloon distal end (80). A perfusion lumen (25) extends through the center of the inner tubing (20) from the perfusion balloon proximal end (75) to the perfusion balloon distal end (80). The inner tubing length (82) can be similar to the outer balloon length (83) or it can be larger or smaller than the outer balloon length (83), both of which can be similar to the perfusion balloon length (85), L. The final perfusion outer balloon diameter (88), D, can be approximately 20-28 mm for aortic valvuloplasty applications. The perfusion outer balloon diameter (88) can be 2-4 mm for coronary artery applications, and can range from 4-15 mm diameter for peripheral vascular or other tubular applications within the body. The inner tubing diameter (89), d, can range from 4 to 15 mm for aortic valve applications. A diameter of 7 mm provides an adequate flow area of approximately 0.4 mm$^2$ to allow for adequate perfusion to the brain for most patients. The inner tubing diameter (89) can range from 2-15 mm for other vascular and non-vascular applications within the body.

An inflation lumen (90) provides inflation fluid through the catheter shaft (92) from a manifold (95) located at the perfusion balloon catheter proximal end (100) and delivered to the annular space (45). A guidewire can extend through the perfusion lumen (25) allowing the perfusion balloon catheter to be introduced into the vasculature in a rapid exchange manner. As an option shown in FIG. 1B, the perfusion balloon catheter can have a separate through-lumen (105) that extends from the manifold (95) to the perfusion balloon catheter distal end (110). This through-lumen (105) can be used to provide passage for a guidewire or for delivery of fluid, drug, or contrast to a position distal to the perfusion balloon (10). Also, optionally shown in FIG. 1B, the perfusion balloon (10) can have an adjunct lumen (115) that extends from the perfusion balloon proximal end (75) to the perfusion balloon distal end (80). This adjunct lumen (115) can be used to provide passage for a guidewire and can be used for rapid exchange for the perfusion balloon catheter. The through-lumen tube (120) and the adjunct tube (125) that extends through the perfusion balloon (10) could be constructed of a polymer that is flexible to allow for length changes that occur during inflation; such materials could include silicone, polyurethane, other thermoplastic elastomers, and copolymers or it can simply be attached only at the proximal end or at the distal end of the perfusion balloon and not change length.

A temporary valve (130) can be located within the perfusion lumen (25). This valve would be formed from a thin and flexible polymer or biological material such that it could be compressed down to a small diameter as the perfusion balloon (10) is being inserted into the body and will unfold to become a functioning valve while the perfusion balloon (10) is expanded. The temporary valve (130) is used, for example, to prevent back flow from occurring from the aorta back into the left ventricle after the heart has ejected blood and is available for filling. Since the perfusion balloon can be used for periods as small as only several minutes or perhaps for hours, the leaflets of the temporary valve (130) could be formed of a smooth polymeric material such as PET, Teflon, nylon, polyurethane, and could be coated with an antithrombotic material such as heparin. The temporary valve (130) can be a simple two leaflet valve similar to that found in the venous vasculature of the body or it can be a single leaflet or a trileaflet valve commonly used in the medical device industry for aortic valves.

During the operation of the present perfusion balloon (10) invention, the perfusion balloon catheter is introduced into the femoral artery or other trans-catheter access site in a small diameter configuration as shown in FIG. 2A. The outer balloon diameter (88) has a smaller initial outer balloon diameter (135), $D_0$, and its length is a longer initial outer balloon length (140), $L_0$. The inner tubing (20) is also at a smaller initial inner tubing diameter (145), $d_0$, and its initial inner tubing length (150) is also relatively longer than after its deployment. Both the initial outer balloon length (140) and the initial inner tubing length (150) are approximately equal to the initial perfusion balloon length (155), $L_0$.

The flexible polymeric coating on the outer balloon (15) and the polymeric coating on the inner tubing (20) can be applied to the braided tubes while they are in this smaller diameter configuration. The perfusion balloon (10) will therein have a tendency to remain in the smaller diameter configuration during introduction into the body. The perfusion balloon (10) is advanced through the aorta or other body member and across the aortic valve leaflets. Upon inflation of the perfusion balloon (10) using saline or contrast medium delivered from the catheter manifold (95), the perfusion balloon (10) will inflate to its final state with a final outer balloon larger diameter, D and shorter perfusion balloon length (83), L as shown in FIGS. 1A and 1B. The inner tubing (20) will also increase in diameter to a larger inner tubing diameter (89), d and a shorter inner tubing length (82), approximately equal to the perfusion balloon length (83), L. The larger diameter of the perfusion lumen (25) will allow blood to be perfused through the perfusion lumen (25) while the outer balloon (15) is in direct contact with the aortic valve leaflets dilating them outwards and allowing for an increased amount of time. The inflation pressure (160) applied to the perfusion balloon (10) will be available to provide the energy needed to cause the flexible outer balloon polymeric surface (50) and the flexible inner tubing polymeric surface (55) to become deformed via stretching, compression, and shear as the balloon is expanded.

It is understood that alternate methods of forming the perfusion balloon are also contemplated. For example, the flexible polymer coatings can be applied with the outer balloon (15) and inner tubing (20) in their expanded configuration or an intermediate configuration. An external sheath could be applied around the perfusion balloon (10) during delivery to maintain it in a smaller diameter configuration state. One alternate embodiment of the perfusion balloon is shown in a large diameter configuration in FIG. 2B and in a small diameter configuration in FIG. 2C. The balloon (15) can be an annular balloon (156) and float freely from the braided balloon filaments (30) and the braided tube fibers (42) of the inner tubing (20). The outer portion (157) of the annular balloon (156) comes into contact and is supported by the braided balloon filaments (30) of an outer tubing (159). The inner portion (158) of the annular balloon (156) comes into contact and is supported by the braided inner tubing fibers (42) of the inner tubing (20). The braided outer tubing (159) and braided inner tubing (20) are attached to each other at the proximal end (75) and distal end (80) of the perfusion balloon. The balloon can be formed from materials commonly used for dilation balloon including polyethylene terephthalate, polyethylene, polyvinylchloride, and others. The annular-shaped balloon (156) is in fluid communication with the inflation lumen (90). In its small diameter configuration shown in FIG. 2C, the annular shaped balloon (156) is folded such that it provides a smaller diameter profile for the perfusion balloon (10). Upon expansion to a larger diameter such as that shown in FIG. 2B, the balloon unfolds to form a fixed larger diameter. The length of the balloon can remain constant, or it can reduce in length due to compression forces placed upon it during length reduction of the perfusion balloon (10). The annular balloon (156) can be attached to the braided balloon filaments (30) or the braided tube fibers (42) at one or more specific individual locations including but not limited to the proximal end (75) or the distal end (80) or the middle of the perfusion balloon (10).

To better understand the operation of this perfusion balloon (10), the following simplified analysis is being presented. The following embodiment that is explained below is only an example of the invention and the invention is not limited to this specific structure. As shown in FIGS. 1A, 1B, 2A-2C, and 3A-3B, as the annular space (45) is filled with inflation fluid, the fluid pressure (160) (P) inside the annular space (45) will increase and apply a downward circumferential expansion balloon force (165), F, on a horizontal plane (170) (see FIGS. 3A and 3B) by the outer balloon (15) to cause the outer balloon to expand in the circumferential direction (175) of: F (exp circ bal),
 where, F (exp circ bal)=P×D×L
 and D is the outer balloon diameter
 and L is the length of the perfusion balloon, approximately equal to the length of the outer balloon and the length of the inner tubing.
This force (165) creates an expansional circumferential stress (180) in the outer balloon wall (56) of σ(exp circ bal)
 where, σ(exp circ bal)=F (exp circ bal)/(2×L×T)
 and T is the outer balloon wall thickness
Since the outer balloon (15) has braided balloon filaments (30) contained within the outer balloon wall at balloon filament angle (35), Theta (θ), a tensile axial force (185), F (tensile axial bal) is generated onto the perfusion balloon (10) end plate acting toward the center of the perfusion balloon (10) to shorten it in length.
 where, F (tensile axial bal)=F (exp circ bal)×cot(θ)
Note: one can see that an axial tensile stress is generated in the outer balloon wall, σ(tensile axial bal):
 where, σ(tensile axial bal)=F (tensile axial bal)/π×D×T
The fluid pressure (160) (P) contained in the annular space (45) also exerts a compressional circumferential force (195) on the inner tubing of, F (comp circ tube), acting to push the horizontal plane (170) upward,
 where, F (comp circ tube)=P×d×L
 and d=the inner tubing diameter
 and L=the length of the inner tubing
This force (195) creates a compressional circumferential stress in the inner tubing wall (58) of: σ(comp circ tube),
 where, σ(comp circ tube)=F (comp circ tube)/(2×L×t)
 and t is the inner tubing wall thickness (59)
Since the inner tubing has braided tube fibers (42) contained within the tubing wall at tubing fiber angle (43), Beta (β), an expansion axial force (200), F (exp axial tube) is generated onto the perfusion balloon (10) end plate acting to axially expand the perfusion balloon (10) to expand it in length.
 where F (exp axial tube)=F (tensile circ tube)×cot(β)
Note: one can see that the axial stress (205) within the tube wall (58) is given by σ(exp axial tube),
 where =F (exp axial tube)/π×d×t
The internal pressure (160) (P) located in the annular space (45) also exerts a force on the perfusion balloon (10) end plate (210), F (exp axial plate), acting to expand the perfusion balloon (10) in an axial direction (40) given by:

$$F(\text{exp axial plate}) = P \times \pi \times \frac{(D^2 - d^2)}{4}$$

This force on the perfusion balloon (10) end plate creates an expansional (tensile) stress (215) in the wall of the outer balloon (15), σ(exp axial bal) and a stress (205) in the inner tubing (20), σ(exp axial tube) that can be described by:
 F (exp axial plate)=σ(exp axial bal)×π×D×T+π(exp axial tube)×π×d×t
Writing a force balance in the axial direction one obtains:

$$L \times D \cot\theta = L \times d \cot\beta + \pi \times \frac{(D^2 - d^2)}{4} \qquad \text{Equation 1}$$

If one takes, for example, specific dimensions for the diameter and length of the outer balloon (15) and inner tubing (20), one is able to identify the parametric variation of values for θ and β that will allow a perfusion balloon (10) to come into equilibrium at those specific diameters and lengths while the perfusion balloon (10) is expanded. The polymeric coating on the braided balloon filaments (30) and braided tube fibers (42) creates a force that must be overcome by the internal inflation pressure (160) as the coatings on the outer balloon (15) and inner tubing (20) polymeric surfaces (50 and 55, respectively) deform during inflation.

For the aortic valve perfusion balloon of the present invention the outer balloon diameter (88) can range from 19-28 mm and is typically 20-26 mm in diameter in order to allow the diseased aortic valve leaflets to be expanded outward against the aortic sinus. The perfusion balloon (10) length could range from 40-80 mm to ensure that the perfusion balloon can center properly across the diseased valve leaflets without displacement of the perfusion balloon due to pressure (160) and flow generated by the left ventricle. The shape of the outer balloon (15) can be cylindrical in general such that positioning the perfusion balloon across the structures of the aortic root and left ventricular outflow tract are not heavily dependent upon axial positioning of the perfusion balloon. The outer balloon (15) of the perfusion balloon (10) of the present invention can also have a dogbone shape to encourage centering of the perfusion balloon across narrowed anatomical features of the left ventricular outflow tract and aortic root while providing favorable dilation characteristics to the valve leaflets. The perfusion lumen (25) should provide approximately 0.3-0.5 cm$^2$ of area for flow of blood to ensure that the brain is supplied with enough oxygen to remain viable. This corresponds to a diameter of approximately 7 mm.

For an aortic valve perfusion balloon having dimension: L=50 mm, D=25 mm, d=7 mm, the following values are obtained for θ and β, using equation 1:

| θ (degrees): | 30 | 45 | 60 | 63 | 70 |
|---|---|---|---|---|---|
| β (degrees): | 11.5 | 23 | 52 | 63 | 89 |

Thus one could braid a perfusion balloon (10) with the above final dimensions such that the balloon filament angle (35) and the inner tubing fiber angle (43) were both 63 degrees with respect to the axis when the perfusion balloon was finally expanded to the above final dimensions. Braiding both the inner tubing (20) and the outer balloon (15) at the same angle may provide the advantage that both the outer balloon and the inner tubing will expand axially and contract diametrically at the same ratio, particularly at the end regions where the outer balloon ends and the inner tubing ends can be attached to each other. It is noted that the braid angle for the outer balloon (15) may vary along its axial length having a different braid angle at its central region in comparison to its proximal or distal ends.

Prior to attaching the outer balloon (15) to the inner tubing (20), the braided outer balloon (15) and braided inner tubing structures would be first elongated axially to make them each reduce in diameter and then coated individually with an elastomeric polymer such that the natural shape of the polymer was consistent with the small balloon diameter and extended axial length configuration of the braid. The braid could be thermally stressed-relieved to provide an equilibrium diameter for the braid in its smaller diameter configuration. The inner tubing (20) and the outer balloon (15) would then be bonded together at the proximal attachment (65) and distal attachment (70). Upon inflation under pressure (160), the outer balloon would expand out until the angles of the braids each reached 63 degrees. The pressure required to accomplish this would be equal to the amount of stress found in the polymer coatings on the inner tubing (20) and the outer balloon (15) as it was stretched under extension, compression, and shear in going from the initial nonstressed state at the smaller diameter to the stressed state at the larger diameter. The perfusion balloon (10) would be held into the smaller diameter state for introduction into the vasculature from the forces generated by the polymeric coatings that resist diametric expansion of the perfusion balloon (10).

Alternately one could braid the outer balloon (15) at 60 degrees and inner tubing (20) with an angle of 52 degrees with the perfusion balloon having the dimensions indicated above. The outer balloon (15) and inner tubing (20) could again be expanded in length, and each braid coated with a polymer. Once the proximal end of the outer balloon (15) is bonded to the proximal end of the inner tubing (20) and similarly for the distal ends, the perfusion balloon (10) would be ready for inflation. The perfusion balloon would again come into equilibrium at the above braided angles as the perfusion balloon was expanded under pressure.

Alternately, one could braid the outer balloon (15) and the inner tubing with angles that are not on the parametric curve (ie, Theta vs Beta) for the chosen values for D and d. In this case the perfusion balloon will tend toward a different outer balloon diameter, inner tubing diameter, and length that satisfies equation 1.

Alternately, one can form the braid for the outer balloon (15) in a smaller initial diameter, $D_0$, if one knows what the final outer balloon diameter (88), D and the desired braid angle, θ, and final length L, that are desired. The relationship between the initial balloon length (140), $L_0$, and the initial diameter, $D_0$ and the initial outer balloon braid angle, $θ_0$ and the final dimensions is given by:

$$D/D_0 = \sin θ / \sin θ_0$$

$$L/L_0 = \cos θ / \cos θ_0$$

$$\frac{\tan θ_0}{\tan θ} = \frac{D_0/D}{L_0/L}$$

Thus one can form a braid for the outer balloon (15) or the inner tubing in the smaller diameter configuration and at a braid angle that will result in a final desired braid angle and final enlarged diameter. The braid for the outer balloon (15) and the braid for the inner tubing can then be coated with a flexible or elastomeric coating in the smaller diameter configuration and allow to cure. The braid for the outer balloon (15) can be coated with a different polymeric coating than that used for the inner tubing. Each braid can then be cured and then attached to each other at the end regions. The perfusion balloon (10) can then be assembled into a perfusion catheter (98).

An advantage exists for providing a braided inner tubing angle that is larger than 45 degrees in order to reduce the amount of force that is acting to cause the inner tubing (20) to expand in length. Also, the braided fiber used for the inner tubing (20) must be large enough in diameter or cross section if flat to resist buckling by the fluid pressure (160) found in the annular space (45). The braided inner tubing fiber must support a stress generated by the in the annular space (45) of:
σ(comp circ tube)=P×d/(2×L)

FIG. 4A-4E describe various energy sources and materials that could be used in conjunction with the present invention. Currently, the existing balloons used for valvuloplasty are inflated for periods of only approximately 8-15 seconds while maintaining the patient on rapid pacing in order to reduce the pressure and flow generated by the left ventricle while the balloon is inflated. The reduced flow is intended to reduce the tendency for the inflated balloon to be forced distally during inflation. The patient is not receiving oxygenated blood flow to the brain during the valvuloplasty procedure. The perfusion balloon (10) of the present invention would allow valvuloplasty or predilitation of the aortic valves prior to TAVI to occur without the need for rapid pacing and would allow the perfusion balloon inflation to proceed for extended periods of time; ie, a few minutes to perhaps 10-30 minutes, and even for an hour in some patients. This extended period of dilatation could allow the viscoelastic structure of the heart valve leaflets to expand to a greater extent that is possible with only a 10-15 second expansions. Additionally, the continual perfusion with the current invention allows a variety of therapeutic modalities to be employed to better expand the valve leaflets. The present invention could provide increased durability to the standard valvuloplasty procedure such that elderly patients with stenotic heart valves would not need to undergo a valve replacement but would be acceptably treated by valvuloplasty alone.

The perfusion balloon (10) of the present invention can also be used to provide perfusion during the dilatation of coronary arteries and grafts used for coronary bypass. In this case the outer balloon (15) could range in diameter from 2.0 mm to 4.5 mm with more typical diameters ranging from 2.5-3.5 mm. The length for coronary balloons can range from 8 mm to more than 25 mm.

Figure 4A:
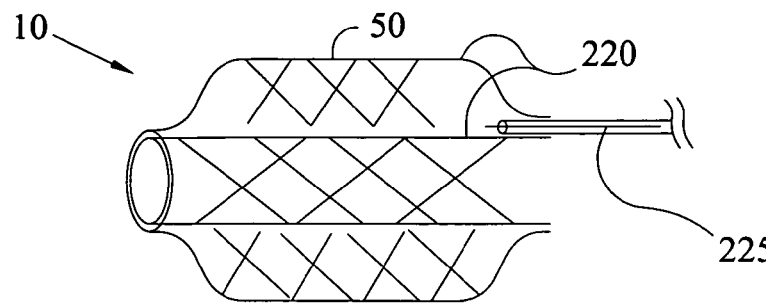
FIG. 4A is a partially sectioned view of an embodiment of the perfusion balloon catheter having a heating element.

FIG. 4A shows the perfusion balloon (10) of the present invention having a heating element (220) such as a resistive heating element (220) placed onto the outer balloon (15) polymeric surface, contained in the balloon filaments (30), contained in the inner tubing wall (58) or placed into the annular space (45) of the perfusion balloon (10). An electrical wire (225) is directed from the manifold (95) to supply energy to the heating element (220). The heating element (220) causes the valve leaflets to soften and reduce the viscoelasticity. The result is that fibrotic attachments can be allowed to stretch more safely. This can be of great value for patients with bileaflet valves that currently have a greater tendency to tear away from the aortic sinus wall resulting in dysfunctional valves or even greater trauma to the patient. Heating the fluid in the annular space (45) to a temperature between 37-50 degrees Celsius would allow the leaflets to stretch and extend in a safer manner and with greater durability over time.

Figure 4B:
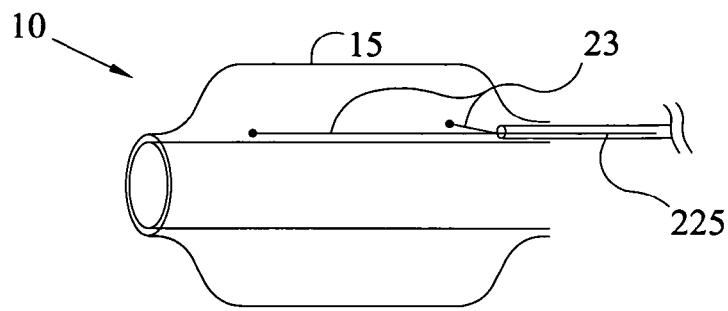
FIG. 4B is a partially sectioned view of an embodiment of the perfusion balloon catheter having a radiofrequency element.

FIG. 4B shows a radiofrequency (RF) element (230) located in the annular space (45) or attached to either the outer balloon (15) on the inside or the outside or the inner tubing (20). The RF element (230) can also be used to heat the fluid within the annular space (45). Alternately, the RF energy can penetrate out into the tissue and be absorbed by the tissue causing the tissue to heat up without creating as much heat in the perfusion balloon itself. The frequency of the RF energy can be tuned to absorb more directly into fibrotic tissue for example in order to more specifically cause this tissue to extend outward under the forces of the outer balloon (15) which is being dilated. The perfusion balloon can be made slightly porous to fluid or ionic flow if desired to obtain a radiofrequency (RF) current flow through the perfusion balloon and into the tissues of the valve that is to be thermally treated.

Figure 4C:
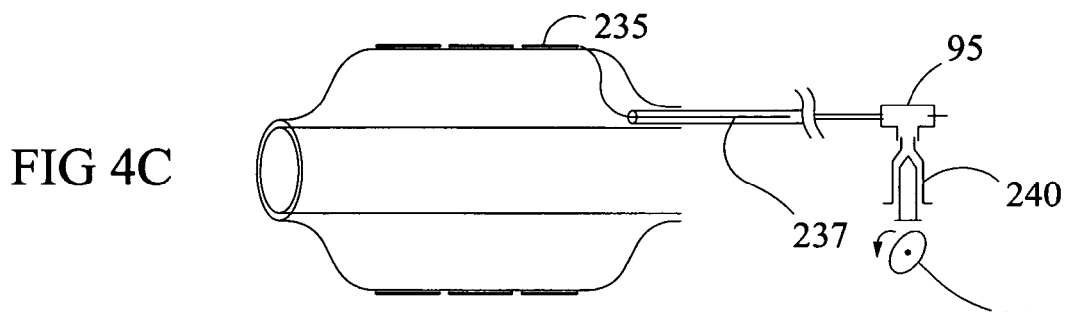
FIG. 4C is a partially sectioned view of an embodiment of the perfusion balloon catheter having ultrasound transducers.

FIG. 4C shows a series of ultrasound transducers (235) or piezoelectric crystals located on or within the outer balloon wall (56) or the inner tubing (20) that cause ultrasound energy to radiate out from the dilated outer balloon (15) and become absorbed into the tissues of the diseased leaflet. The ultrasound energy can be used to break up calcified deposits. Also, the ultrasound energy of a lower frequency can penetrate more deeply into the fibrotic leaflet tissue to cause either denatuation or heating of the tissue. This tissue modification by the ultrasound energy combined the forces of the expanding outer balloon (15) will allow the aortic valve leaflets to expand outward and become more fixed in the new configuration, with enhanced durability of the valvulolasty procedure. The ultrasound transducer (235) is powered by an electrical source via energy delivered from an electrical wire (237) from the manifold (95).

An alternate way of providing improved expansion to calcified or fibrotic tissue found in a tubular member of the body is to provide pressure pulses to the perfusion balloon in rapid succession. Such pulses can range in amplitude from 1 to 4 atm for a valvuloplasty perfusion balloon (10) and from 1 to over 10 atm for a coronary artery perfusion balloon (10). The pressure or vibration cycle frequency can range from 1 to several hundred cycles per second. Such pulses can be generated from an external source connected to the inflation lumen (90) located on the manifold (95) as shown in FIG. 4C. The pressure generator can be a positive displacement pump (240) such as a piston pump operated by a cam (245) that cycles the pressure within the perfusion balloon (10).

Figure 4D:
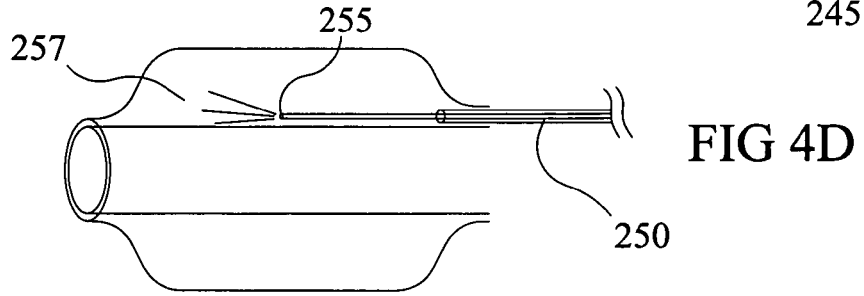
FIG. 4D is a partially sectioned view of an embodiment of the perfusion balloon catheter having an orifice to deliver cryogenic material.

FIG. 4D shows the perfusion balloon (10) of the present invention with small tubing (250) extending into the annular space (45). The tubing (250) has an orifice (255) near its distal end. A cryogenic material (257) such a nitrous oxide or carbon dioxide is converted from a liquid to a gas as it passes through the orifice (255) causing the fluid to cool down dramatically via the joule-kelvin effect. The cooling of the aortic valve leaflet to approximately zero to −10 degrees Celsius causes multiple microfractures to occur in the valve leaflet tissue as it is expanded outward by the outer balloon (15). Balloon expansion can occur for several seconds up to several minutes. The microfractures allow the valve leaflet to tear in multiple micro tears and result in a safer and more durable valvuloplasty procedure.

Figure 4E:
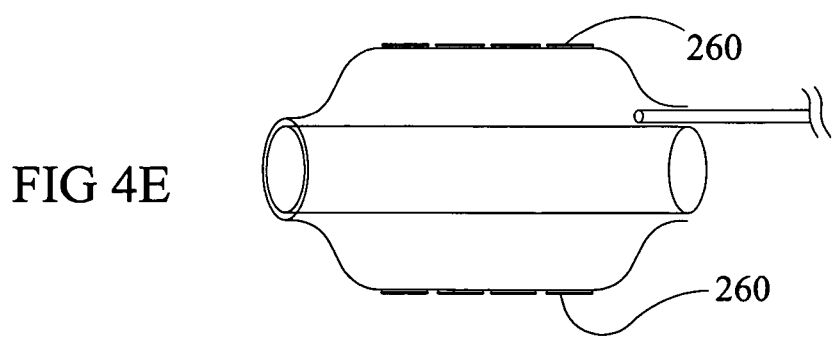
FIG. 4E is a partially sectioned view of an embodiment of the perfusion balloon catheter having a drug loaded on the outer surface of the balloon.

FIG. 4E shows the application of a drug (260) to the outside surface of the perfusion balloon (10). The drug (260) can be an anticalcification drug such as EDTA or many of its derivatives or it can be an antirestenotic drug such as Taxol or Sirolimus, or it can be an anti-inflammatory or anti thrombotic drug. The delivery of the drug (260) directly to the diseased leaflets will allow the leaflets to remain functional following the valvuloplasty procedure by reducing the tendency to recalcify, or by reducing the tendency for thrombosis which can lead to calcification, or by preventing cellular migration onto the leaflets or colonization of cells on the leaflets which also can lead to formation of calcification. The present invention allows direct application of such drugs (260) onto the leaflets for extended periods of time while the perfusion balloon is inflated so that the drug (260) has time to become absorbed into the leaflet tissues.

Figure 5A:
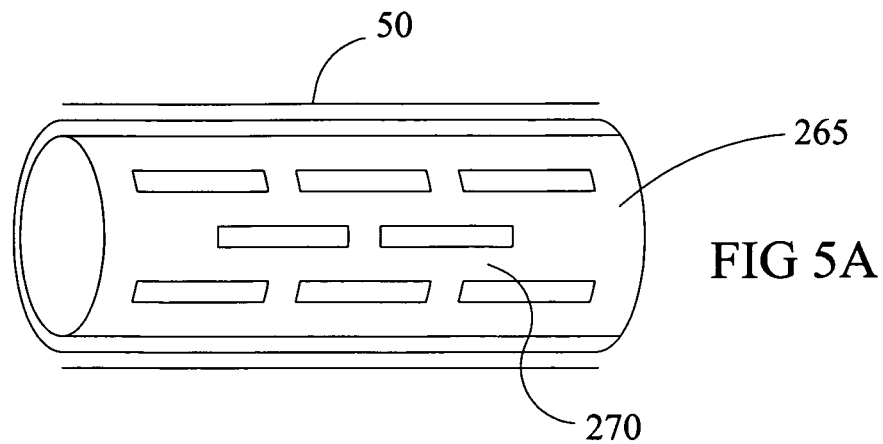
FIG. 5A is a perspective view of a slotted tube structure for the outer balloon or inner tubing in a small diameter non-expanded configuration.
Figure 5B:
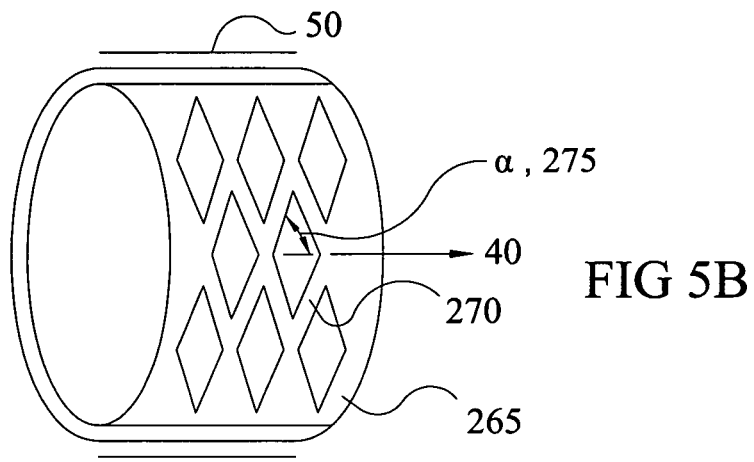
FIG. 5B is a perspective view of a slotted tube structure for the outer balloon or inner tubing in a larger diameter expanded configuration.
Figure 5C:
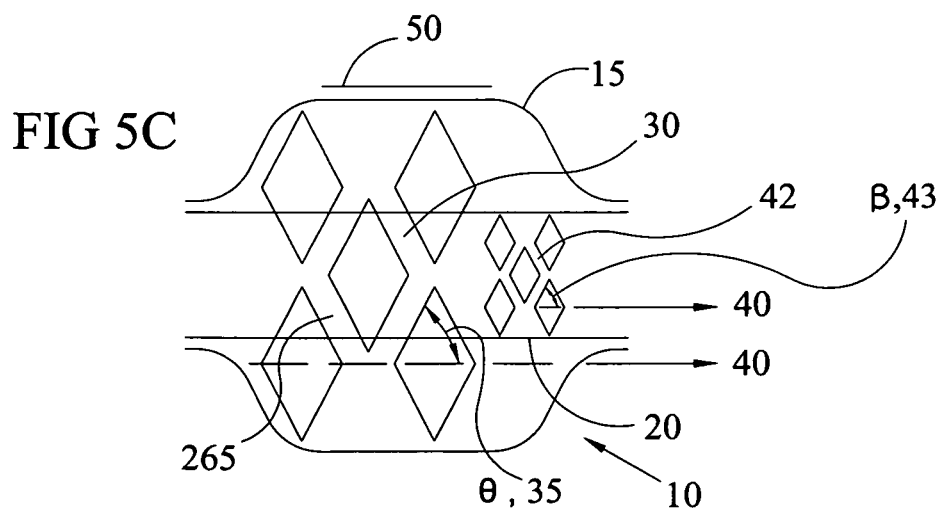
FIG. 5C is a partially sectioned view of an embodiment of the perfusion balloon in an expanded configuration having an outer balloon with filaments and an inner tubing with tube fibers.

An alternate embodiment for the structure for the outer balloon (15) or the inner tubing (20) is shown in FIGS. 5A-5C. FIG. 5A shows an expandable member (265) in a smaller diameter configuration and FIG. 5B shows the expandable member (265) in an expanded larger diameter configuration. In the expanded configuration as shown in FIG. 5B, the fiber/filament (270) has a fiber filament angle (275), $\alpha$, with respect to the axial direction (40); this angle (275) can represent the fiber angle (43), $\beta$, or the filament angle (35), $\theta$, as shown in FIG. 5C. The expandable member (265) can be used instead of the braided structure described earlier for the outer balloon (15) or can be used instead of the braided structure described earlier for the inner tubing. The expandable member (265) can be formed from a metal tubing such as nitinol, stainless steel, elgiloy, or other thin-wall metal tubes. A variety of machining methods can be used to form the fibers/filaments of the expandable member (265) including laser, EDM, electrochemical etching, or standard machining. The expandable member (265) can also be formed from a plastic tubing via machining methods or by molding. Other configurations are anticipated for the expandable member (265) and the configurations shown in FIGS. 5A and 5B are intended to serve as an example of a machined tube used to form a perfusion balloon (10).

FIG. 5C shows the application of the expandable member (265) to the perfusion balloon (10). The outer balloon (15) has balloon filaments (30) that are formed with a filament angle (35), $\theta$, with respect to the axial direction (40) in the expanded configuration. The inner tubing (20) has tube fibers (42) that are formed with a fiber angle, $\beta$ with respect to the axial direction (40). An outer balloon polymeric surface (50) and an inner tubing polymeric surface (55) are applied using materials and methods similar to that described for the embodiment of FIGS. 1A and 1B. Application of fluid pressure (160) to the annular space (45) between the outer balloon (15) and the inner tubing (20) causes the outer balloon (15) to expand from a smaller diameter configuration to an expanded larger diameter configuration shown in FIG. 5C. The outer balloon (15) places a force on the inner tubing (20) as described earlier for the braided structures for the outer balloon (15) and inner tubing (20) causing the inner tubing (20) to reduce in length and enlarge in diameter forming the configuration as shown in FIG. 5C.

The thickness of the balloon filaments (30) for the outer balloon (15) shown in FIG. 5C can be very thin, ranging from 0.001-0.004 inches. The thickness of the tube fibers (42) used to form the inner tubing (20) shown in FIG. 5C should be thick enough to support the internal pressure (160) within the annular space (45) between the outer balloon (15) and the inner tubing (20); the wall thickness (59) could range from 0.002-0.008 inches.

As stated earlier, the actual detailed structure of the expandable member (265) can attain any orientation of the fibers or filaments that allows the expandable member (265) to expand in diameter while reducing in length and provide the structural strength as described earlier. One embodiment of the expandable member (265) made from a machined tube that is intended for use as the inner tubing (20) is shown in FIG. 5D. In this embodiment a structural tube fiber (280) that is directed with significant componency in the circumferential direction (175) is intended to provide the column strength needed to force the inner tubing (20) into a larger diameter as the outer balloon (15) wall reduces in length during expansion. This structural tube fiber (280) also provides strength to resist collapse of the inner tubing (20). A non-structural hinged tube fiber (285) that is directed in an opposed direction. The width of the hinged tube fiber (285) has been reduced by the presence of hinges (290), thereby allowing the hinged tube fiber (285) to flex at the location of the hinge (290) while it is being supported by the structural tube fiber (280).

The invention claimed is:

1. A catheter having a distal end and a perfusion balloon positioned near said distal end, said perfusion balloon having an outer tubing with angled filaments contained within, and an inner tubing positioned adjacent said outer tubing, said inner tubing having angled fibers contained within, said outer tubing being attached to said inner tubing at an open proximal end and at an open distal end of said perfusion balloon forming an annular space between said outer tubing and said inner tubing, said open proximal end and said open distal end providing passage for fluid through said inner tubing from said open proximal end to said open distal end; said outer tubing and said inner tubing being expandable from a smaller diameter delivery state to a larger diameter final state.

2. The catheter of claim 1 wherein said angled filaments form a braided outer tubing and said angled fibers form a braided inner tubing.

3. The catheter of claim 1 wherein said tubing and said inner tubing are formed with flexible polymeric material that is a fluid-tight barrier.

4. The catheter of claim 3 having an equilibrium condition in said smaller diameter delivery state wherein said fluid-tight barrier is formed without axial or circumferential stress.

5. The catheter of claim 3 wherein said fluid-tight barrier is formed with axial stress contained therein in the larger diameter final state.

6. The catheter of claim 5 wherein said outer tubing and said inner tubing get larger in diameter upon exposure of said annular space between said outer tubing and said inner tubing to an inflation pressure.

7. The catheter of claim 3 wherein said angled filaments are braided with a filament angle and said angled fibers are braided with a fiber braid angle, said filament angle and said fiber braid angle in the larger diameter final state forming an equilibrium final shape for perfusion balloon diameter, perfusion balloon length, and inner tubing diameter wherein axial forces are in balance.

8. The catheter of claim 3 wherein said filaments are braided with a filament angle and said angled fibers are braided with a fiber braid angle, said filament angle being approximately equal to said fiber braid angle in the larger diameter final state.

9. The catheter of claim 3 wherein said balloon filaments are braided with a filament angle and said angled fibers are braided with a fiber braid angle, said filament angle being approximately equal to said fiber braid angle in the smaller diameter delivery state.

10. The catheter of claim 3 wherein said angled fibers are braided with a fiber braid angle, said fiber braid angle being greater than 45 degrees in the larger diameter final state.

11. A catheter for providing dilation to a stenotic region of a tubular member of a body, said catheter having a balloon positioned at its distal end and a manifold in fluid communication with said balloon at the proximal end of said perfusion catheter, said catheter comprising;

A. a balloon having an outer portion that is in contact with angled filaments, said angled filaments forming an outer tubing, B. said balloon having an inner portion that is in contact with angled fibers, said angled fibers forming an inner tubing, C. said balloon being formed from one or more polymers that form a fluid-tight barrier, D. said inner tubing being attached to said outer tubing at a proximal end and distal end of said balloon, E. said balloon configured to be delivered into the tubular member of the body in a smaller diameter state and expandable to a larger diameter state, F. said inner tubing having an open proximal end and an open distal end, said inner tubing forming a perfusion lumen for blood flow through said balloon.

12. The balloon of claim 11 wherein said angled filaments are braided filaments and said angled fibers are braided fibers.

13. The catheter of claim 11 wherein said balloon is approximately 19-28 mm in diameter to dilate stenotic aortic valve leaflets and provide perfusion from a left ventricle to an aorta of the body during dialation of the stenotic aortic valve leaflets.

14. The catheter of claim 11 wherein said balloon is formed from a polymer that resists further diameter expansion beyond a specified diameter.

15. The catheter of claim 11 further comprising an energy source means to enhance a valvuloplasty procedure.

* * * * *